United States Patent [19]

Little

[11] Patent Number: 5,075,430
[45] Date of Patent: Dec. 24, 1991

[54] PROCESS FOR THE PURIFICATION OF DNA ON DIATOMACEOUS EARTH

[75] Inventor: Michael C. Little, Martinez, Calif.

[73] Assignee: Bio-Rad Laboratories, Inc., Hercules, Calif.

[21] Appl. No.: 629,787

[22] Filed: Dec. 18, 1990

Related U.S. Application Data

[63] Continuation of Ser. No. 288,515, Dec. 12, 1988, abandoned.

[51] Int. Cl.$^5$ .................. C07H 21/00; C07H 21/04
[52] U.S. Cl. .................................. 536/27; 536/28; 536/29; 536/127; 435/803; 423/335
[58] Field of Search ................... 935/19; 536/27; 423/335; 435/803

[56] References Cited

U.S. PATENT DOCUMENTS

| | | | |
|---|---|---|---|
| 4,153,661 | 5/1979 | Ree et al. | 264/120 |
| 4,921,952 | 5/1990 | Longmire et al. | 536/27 |
| 4,923,978 | 5/1990 | McCormick | 536/27 |

OTHER PUBLICATIONS

H. Birnboim, Meth. in Enzym., vol. 100, pp. 243–255. (1983).
M. Marko et al., Analy. Biochem. 121, pp. 382–387 (1982).
B. Vogelstein et al., Proc. Natl. Acad. Sci. USA. vol. 76, No. 2, pp. 615–619, (Feb. 1979).
K. Nugent et al., Journal of Virology. vol. 21, No. 3, pp. 1061–1073 (Mar. 1977).
N. S'yakste et al. Analysis of Cell Nucleoproteins by Method of Nucleoprotein–Celite Chromatography, 1982 Plenum Publishing Corp. pp. 1022–1028.
N. S'yakste et al. Analysis of Cellular Nucleoprotein with Nucleo-Protein–Celite Chromatography. 1986 Plenum Publishing Corp. pp. 1007–1016.
T. Maniatis et al., Eds. Molecular Cloning. Cold Spring Harbor Lab. 1982, p. 504.
Colpan et al., 1984 J. Chromatog. 296:339–353.
Moreau et al., 1987, Analyt. Biochem. 166:188–193.
Ausubel et al., Eds. Current Protocols in Molecular Biology, John Wiley & Sons, 1987, pp. 1.7.5–1.7.7.
Holmes et al., 1981, Analyt. Biochem. 114:194–197.
Maniatis et al., Edgs. Molecular Cloning, Cold Spring Harbor Lab., 1982, pp. 90∝91.

Primary Examiner—John W. Rollins
Assistant Examiner—Gary L. Kunz
Attorney, Agent, or Firm—Townsend and Townsend

[57] ABSTRACT

This invention is directed to a process for the purification of plasmid and other DNA, both single-stranded and double-stranded, by immobilizing the DNA onto diatomaceous earth in the presence of a chaotropic agent and eluting the DNA with water or low salt buffer. The resulting purified DNA is biologically active. Also included in the invention is a process for the immobilization of DNA onto diatomaceous earth in the presence of a chaotropic agent.

6 Claims, 1 Drawing Sheet

PROCESS FOR THE PURIFICATION OF DNA ON DIATOMACEOUS EARTH

This application is a continuation of application Ser. No. 07/288,515 filed Dec. 12, 1988, now abandoned.

BACKGROUND OF THE INVENTION

The present invention is related to the purification of plasmid and other DNA.

The purification of plasmid DNA from bacterial lysates is a rate-limiting and time-consuming step in molecular biology. The preparation of plasmid DNA for cloning and other purposes generally follows the scheme established in Birnboim (1983, Methods in Enzymology 100:243-255) in which the cleared bacterial lysate is applied to a cesium chloride gradient and centrifuged for 4-24 hours. This is usually followed by the extraction and precipitation of the DNA to yield DNA that is sometimes, but not always, free of RNA, protein and chromosomal DNA. Other methods employing cleared lysates to prepare DNA of similar quality are ion exchange (Colpan et al., 1984, J. Chromatog. 296:339-353) and gel-filtration (Moreau et al., 1987, Analyt. Biochem. 166:188-193) high-performance methods. While these latter methods generally work well as alternatives for ScCl gradients, they require costly solvent delivery systems and the reprecipitation of the isolated DNA fractions since they usually contain salt or are too dilute, and are limited in the amount of DNA that can be prepared (<500 μg) per run. Since typically 1 liter cultures of *E. coli* yield >2 mg of plasmid DNA plus much RNA and protein, the capacity of the high performance methods requires multiple cycles to process these quantities of DNA.

It was discovered by Marko et al. (1981, Analyt. Biochem. 121:382-387) and Vogelstein et al. (1979, Proc. Nat. Acad. Sci. 76:615-619) that when DNA-containing extracts were applied in high concentrations of sodium iodide or sodium perchlorate, the DNA alone will bind to ground scintillation vials or ground GF/C glass fiber disks. RNA and protein do not bind. The bound DNA will elute eventually in water. It was also reported that DNA does not bind to and thus cannot be purified using other fine silicas such as silica gel and porous glass beads (Vogelstein, supra). A product, GENECLEAN TM (Bio 101, La Jolla, Calif.), is now commercially available for the purification of DNA which includes ground glass slurry, saturated NaI and 50% ethanol wash buffer.

Diatomaceous earth has been used for filtration, in chromatography and as an abrasive. With respect to DNA, diatomaceous earth has been used to separate cell wall fragments of Streptococcal cell lysates from which bacteriophages are prepared (Nugent et al., 1977, J. Virol. 21:1061-1073). No adsorption and release of DNA was involved. It has also been used in "nucleoprotein-Celite chromatography", which uses lysed nuclei adsorbed to Celite ® (a commercial form of diatomaceous earth) and denaturing conditions and temperature to release the cellular DNA from the protein (S'Yakste et al., 1981, Mol. Biol. (Mosc.) 15:1321-1329; 1985, Mol. Biol. (Mosc.) 19:1231-1241). The protein itself is irreversibly adsorbed onto the Celite, while the nucleic acids do not interact with the Celite.

Thus, a method was still desired to rapidly and inexpensively separate and purify DNA that was also amenable to scale-up.

SUMMARY OF THE INVENTION

It has now been found that diatomaceous earth is useful for the purification of plasmid and other DNA by immobilizing the DNA onto the diatomaceous earth particles in the presence of a chaotropic agent, followed by elution of the DNA with water or low salt buffer.

DETAILED DESCRIPTION OF THE INVENTION

Figure 1:
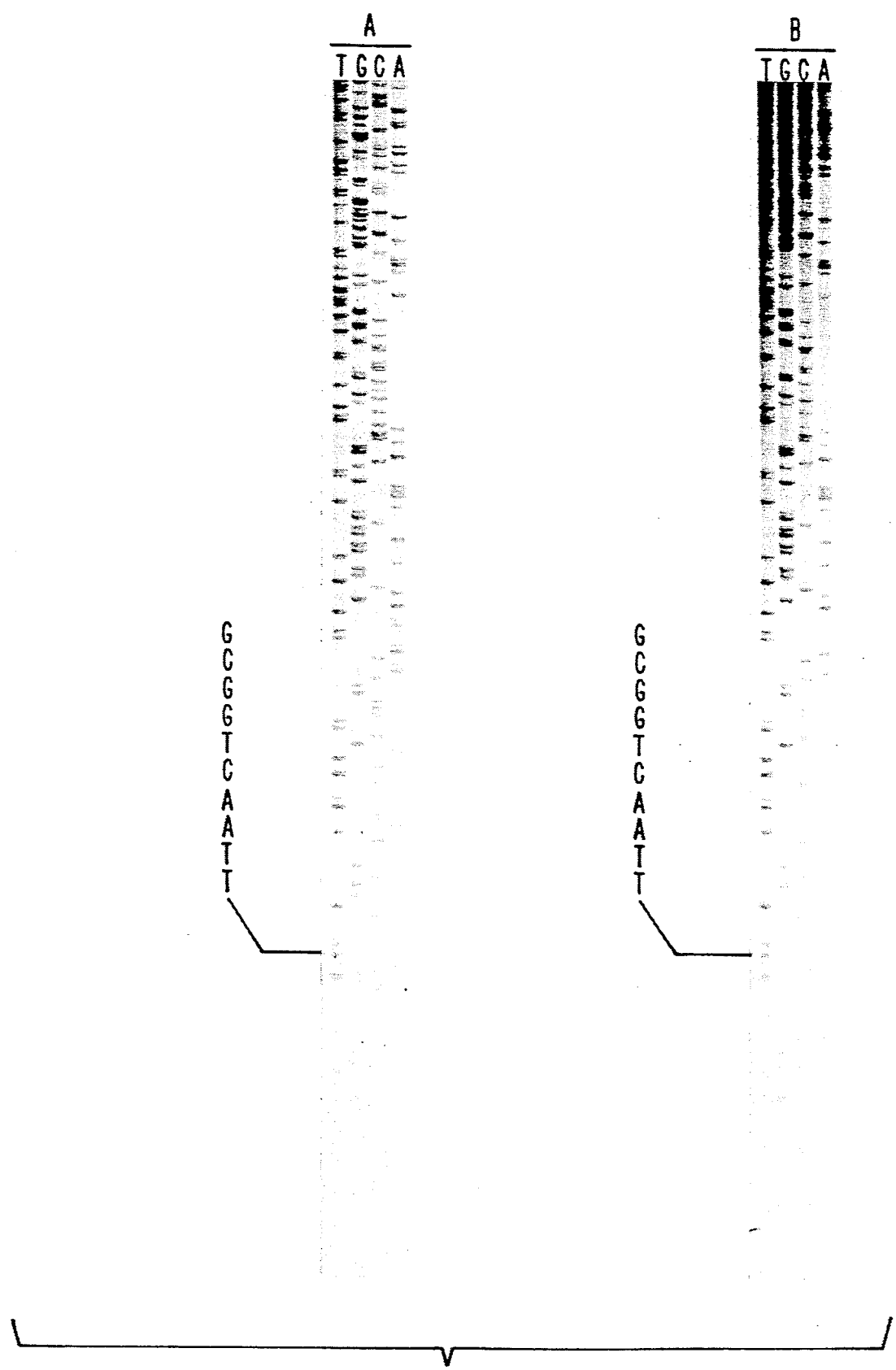
FIG. 1 shows the ampicillin resistance (amp) gene in two gels of directly sequenced DNA, gel A being pBR322 purified by two sequential CsCl gradients as in the prior art and gel B being pRSVcat purified by the process of the present invention.

This invention is directed to a process for the purification of plasmid and other DNA, both single-stranded and double-stranded, by immobilizing the DNA onto diatomaceous earth particles and eluting the DNA with water or low salt buffer. The resulting purified DNA is biologically active.

More particularly, the present invention is a process for the purification of plasmid DNA which comprises
a) immobilizing the DNA onto diatomaceous earth in the presence of a chaotropic agent;
b) washing the resulting diatomaceous earth-bound DNA with an alcohol-containing buffer;
c) removing the alcohol-containing buffer; and
d) eluting the DNA in a low salt buffer or in water.

In another aspect, the invention is directed generally to the immobilization of DNA onto diatomaceous earth which comprises contacting the DNA with the diatomaceous earth in the presence of a chaotropic agent. Such immobilized DNA may or may not later be released, depending on the use contemplated, by elution with water or a low salt buffer. Such immobilization is desirable in that it makes the DNA available for a number of manipulations, treatments or uses. For example, the DNA may be treated or reacted with a reagent, or it may be used in a diagnostic procedure such as a binding assay.

Diatomaceous earth, also known as kieselguhr or diatomite, is a loosely coherent chalk-like sedimentary rock made up mainly of fragments and shells of hydrous silica secreted by diatoms, microscopic one-celled algae. The particles are very fine and have high surface area. Silica content may be as high as 94%. Because of the intricate structure of the diatom skeletons that form diatomaceous earth, the silica has a very different physical structure from other forms in which it occurs.

Diatomaceous earth is available commercially in three forms: natural, calcinated and flux-calcinated. Calcinated diatomaceous earth is diatomaceous earth treated by high temperature calcination at about 980° C. Flux-calcinated diatomaceous earth is prepared by the calcination of the natural product in the presence of flux, generally soda ash although sodium chloride may be used. This treatment reduces the surface area of the diatom particles, changes the color from the natural buff to white and makes any impurities present insoluble. Flux-calcinated diatomaceous earth may be obtained commercially as Celite ® (Johns-Manville Products Corp., Lompoc, Calif.). It is also readily available from other producers. All forms of diatomaceous earth may be used in this invention. Flux-calcinated diatomaceous earth is preferred.

Diatomaceous earth is available in different particle sizes. The size of the particles is not critical in the practice of the present invention, although the absorption capacity tends to decrease as the particle size increases, particularly with particles which are >125 μm. Examples of diatomaceous earth include Celite 560, with an average particle size of 106 μm; Celite 545, with an average particle size of 45 μm; and Celite Super-Fine Super Floss, with an average particle size of 4 μm. The size of particle chosen will be dependent primarily on such things as commercial or processing factors. These include cost of the material, and the binding or processing time. The average particle size is conveniently less than 125 μm, and is preferably of about 50 μm or less, more preferably of about 1 μm to about 10 μm.

The diatomaceous earth may be utilized in this invention as an aqueous slurry, in an entrapped membrane format, or as packing material in a column or other fritted barrier.

The correct volume of diatomaceous earth slurry should be added for complete binding and is dependent on the DNA binding capacity of the particular diatomaceous earth utilized and on the volume ratio of diatomaceous earth to water in the slurry. For example, the capacity of Celite Super-Fine Super Floss diatomaceous earth (average particle size=4 μm) is ca. 2 mg DNA per gram diatomaceous earth. The preferred Super-Fine Super Floss slurry would be 167 mg of diatomaceous earth per mL of water.

One example of an entrapped membrane format is a composite sheet prepared by the distribution of the diatomaceous earth particles in a matrix of inter-entangled polytetrafluoroethylene fibrils, following the method disclosed in U.S. Pat. No. 4,153,661.

A chaotropic agent is a substance that enhances the partitioning of nonpolar molecules from a nonaqueous to an aqueous phase as a result of the disruptive effect that the substance has on the structure of water. Examples of chaotropic agents include sodium iodide, sodium perchlorate and sodium trichloroacetate. The chaotropes may be used singly or as mixtures of two or more chaotropes.

DNA of 200 bp and greater will bind selectively to diatomaceous earth in a high concentration of a chaotropic agent, while proteins, RNA, small DNA linkers used in cloning and nucleoside triphosphates will not. Both single-stranded and double-stranded DNA may be bound in this manner, including supercoiled DNA of up to at least 16 Kb.

In addition, agarose gels can be dissolved readily in chaotropes, such that DNA bands from gels may also be recovered. This is a great improvement over the traditional methods of recovery of DNA fragments from agarose, such as electroelution or "crush and soak" methods. Such previous methods are long and tedious. Additionally, the recovery of DNA fragments with the present invention allows direct cloning from specific fragments, in lieu of "shotgun cloning" of a mixture of unresolved fragments. It also makes possible the isolation of a specific fragment. It is not necessary that the agarose be of low melting point grade.

The chaotropic agent may be used as is or it may conveniently be in a buffer. One example of such a buffer comprises: 6.0 M sodium perchlorate. 0.05 M Tris-Cl pH 8, and 10.0 mM ethylenediaminetetraacetic acid (EDTA). This buffer will be abbreviated herein as "NaClO$_4$ binding buffer".

In order to obtain complete immobilization of DNA, it is desirable to have a ratio of at least two volumes of chaotrope binding buffer per volume of slurry plus DNA solution. A ratio of three to four volumes is preferred.

The alcohol in the alcohol-containing buffer is selected from the lower alcohols such as methanol, ethanol and isopropanol. It is convenient to use ethanol in the present invention because many enzymes will tolerate traces of this solvent and because samples eluted with TE low salt buffer (which may contain a trace of ethanol) may be readily freed of this solvent by gentle vacuum. Higher alcohols tend to be more oily and difficult to remove by gentle vacuum treatment. The alcohol is present in the buffer at a volume of from about 20% to about 95% (v/v). At volumes below about 20% alcohol, the DNA is released. The alcohol-containing buffer may or may not contain a salt such as sodium chloride. The salt is apparently not necessary for the buffer to perform effectively.

An example of an alcohol-containing wash buffer comprises: 20.0 mM Tris-Cl pH 7.5, 2.0 mM EDTA, 0.4 M NaCl, and 50% v/v ethanol. This buffer will be abbreviated herein as "50% ethanol buffer" or "50% washing buffer".

In order to lower the RNA and protein concentrations in plasmid lysates, it is necessary to perform a sufficient number of washes using the chaotrope binding buffer and the 50% washing buffer. The amount of RNA and protein remaining is indirectly proportional to the number of volume washes performed on the diatomaceous earth pellet, membrane or column. Generally, about three washes of each buffer is sufficient to lower the RNA and protein concentrations to acceptable levels.

The efficiency of release of immobilized DNA from the diatomaceous earth pellet, membrane or column will be proportional to the ratio of the volume of low-salt buffer or water added to the volume of the pellet, membrane or column. Thus, with a 5 μL diatomaceous earth pellet, for example, 5 μL of buffer or water (1 volume) will extract about 50% of the DNA. Likewise, 10 volumes of buffer or water added per volume of pellet will permit the recovery of >90% of the DNA. However, it should be kept in mind that the more buffer or water added, the more dilute the eluted DNA. Therefore, the volume of buffer or water chosen will be dependent on the particular needs and uses of the eluted DNA. It is also possible to perform consecutive elutions of the pellet in order to obtain a higher yield with minimal dilution. Thus, for example, two consecutive elutions of the diatomaceous earth pellet using 2 volumes each of buffer or water equal to 1 volume of the pellet will permit about 70% recovery with minimal dilution.

One example of a low salt buffer comprises: 10.0 mM Tris-Cl pH 8, and 1.0 mM EDTA. This buffer will be abbreviated herein as "TE".

The general procedure for the isolation of DNA from agarose gel slices using the process of the present invention is as follows. The DNA samples should be loaded into the wells of an agarose gel using glycerol (2 μL 80% glycerol per 18 μL sample/well) rather than loading dyes. These dyes may possibly cause problems in trying to cut, clone, or nick-translate the isolated fragment. A marker sample containing dye can be run in adjacent lanes to monitor the progress of the electrophoresis. Gels are typically run in Tris-borate-EDTA (TBE) buffer, but Tris-acetate-EDTA (TAE) buffer will also work. At the end of the run, the gel is placed into a solution of 1 μg/mL ethidium bromide and is stained for ca. 10 minutes. The gel may be rinsed briefly in deionized water and the band(s) of interest located with a UV trans-illuminator. The desired band is carefully excised and is microfuged for several seconds to sediment the gel plug. Two to five (preferably three to four) volumes of chaotrope binding buffer are added to the gel plug and the mixture is vortexed to resuspend. The microfuge tube is kept at 37°-55° C. for several minutes to assist the dissolution of the agarose. This can best be accomplished by intermittent vortexing of the sample through the incubation time. Diatomaceous earth slurry is added at a volume not to exceed 50 μL. If more is needed on the basis of the amount of DNA present, the amount of chaotrope binding buffer is increased. The mixture is incubated 5-15 minutes at room temperature with intermittent or continuous mixing. The sample is then microfuged for 30 seconds. The supernatant is discarded, the pellet (containing the bound DNA) is washed by quickly vortexing to resuspend using 1 ml of chaotrope binding buffer, and the suspension is microfuged as above. This washing procedure is then repeated. The supernatant is discarded and the pellet is washed using two or three 1 ml washes of 50% washing buffer. After the last wash, all traces of liquid in the tube are removed, especially that around the pellet. A pipet tip could be used for this removal. A volume of TE or water that is three or more times that of the diatomaceous earth pellet is added, and the suspension is incubated at room temperature for 5 minutes, after which it is microfuged for 30 seconds. The DNA is found in the supernatant and should be carefully removed without disturbing the pellet. The DNA can be transferred to a fresh tube and microfuged for 5 minutes to remove the last traces of diatomaceous earth, although removal of the last traces of silica is not crucial, since this has not been found to affect the transformability or restrictability of the DNA. The recovered DNA is ready to use. Bands retrieved by this method exhibit high recovery (>90%). transform cells at a very high frequency, and cut and ligate well.

Plasmid DNA from mini-prep lysates can be purified using the process of the present invention. Lysis methods which work with this process include Triton-Lysozyme Lysis (Ausubel et al., eds., *Current Protocols in Molecular Biology*, John Wiley & Sons, 1987, pp. 1.7.5-1.7.7), Triton Lysis-Boiling (Holmes et al., 1981. Analyt. Biochem. 114:193-197) and the cleared lysate method employing SDS/NaOH (Maniatis et al., eds., *Molecular Cloning*, Cold Spring Harbor Laboratory. 1982. p. 90), the disclosures of each of which are incorporated herein by reference. The amount of RNA contamination occurring will depend on the number of chaotrope and ethanol washes used. If using the cleared lysis method, the process of the invention will begin with a nucleic acid pellet (usually the first isopropanol pellet is adequate). If using the boiling method or the lysozyme method, the process may begin with a resuspended nucleic acid pellet or with the supernatants derived from the centrifugation step used to eliminate the cellular debris. If dried nucleic acid pellets are used, they are resuspended well in TE or water, and any clumps of undissolved protein are centrifuged out. The amount of diatomaceous earth slurry needed is determined, using the capacity of the diatomaceous earth for DNA and the ratio of diatomaceous earth to water in the slurry. To the DNA sample is added a quantity of chaotrope binding buffer to equal two to five (preferably three to four) times the combined volume of the slurry and the DNA solution. The slurry is then added to the DNA and buffer. The suspension is incubated at room temperature for 15 minutes with mixing and is then microfuged for 30 seconds. The supernatant is discarded, the pellet (containing the bound DNA) is washed by quickly vortexing to resuspend using 1 ml of chaotrope binding buffer, and the suspension is microfuged as above. This washing procedure is then repeated. The supernatant is discarded and the pellet is washed using three 1 ml washes of 50% washing buffer. After the last wash, all traces of liquid in the tube are removed, especially that around the pellet. A pipet tip could be used for this removal. A volume of TE or water that is three or more times that of the diatomaceous earth pellet is added, and the suspension is incubated at room temperature for 5 minutes, after which it is microfuged for 30 seconds. The DNA is found in the supernatant and should be carefully removed without disturbing the pellet. The DNA can be transferred to a fresh tube and microfuged for 5 minutes to remove the last traces of diatomaceous earth, although removal of the last traces of silica is not crucial, since this has not been found to affect the transformability or restrictability of the DNA. The recovered DNA is ready to use.

In order to isolate semi-preparative amounts of plasmid (that is, plasmid in the range of 100-400 μg) using the above procedure, a large amount of chaotrope binding buffer and of 50% washing buffer would be used and the DNA may be eluted somewhat dilute for efficient release. Additionally, longer centrifugation times would be required due to the increased acceleration/deceleration times needed with a larger centrifuge. The following modification of the above procedure makes the process more convenient when used with large amounts of material. The nucleic acid pellet is resuspended in TE or water, after which the appropriate volume of chaotrope binding buffer and diatomaceous earth slurry are added based upon the capacity of the slurry and the volume of buffer needed. The suspension is incubated for 15 minutes with occasional or constant mixing. A 25 mm Teflon 0.45 μm filter cartridge (model #343-0001, Bio-Rad, Richmond, Calif.) is washed with 2-3 mL of chaotrope binding buffer and the washes are discarded. The slurry is transferred to a syringe and is pushed through the filter at a constant flow rate. The filter-trapped diatomaceous earth is washed with 10 mL of chaotrope binding buffer and then with 10 mL of 50% washing buffer. Using the syringe, several bursts of air are purged through the filter to remove any trapped washing buffer. The DNA is then eluted with low salt buffer or water, which may be collected in fractions or in one tube. It is possible to view the elution of the plasmid by observing the Schlieren effect in solution as the DNA solution comes through. The recovered DNA is ready to use.

Alternatively, larger amounts of plasmid may be isolated by use of a membrane system wherein the diatomaceous earth is entrapped within the membrane prior to its coming into contact with the DNA. The membrane containing the diatomaceous earth is washed with about 5 mL of chaotrope binding buffer and the washes are discarded. Chaotrope binding buffer (three volumes) is added to the resuspended nucleic acid pellet and the solution is then applied to the membrane-bound diatomaceous earth by syringe at a flow rate of about 1 mL/minute. The membrane is then washed with chaotrope binding buffer and with washing buffer. To remove traces of the latter buffer, the membrane is purged by an air-filled syringe until no more liquid emerges. The DNA is eluted with low salt buffer or water using a syringe.

The process of the present invention is further illustrated by the following examples. These examples are offered strictly for purposes of illustration, and are not intended to either limit or to define the invention.

EXAMPLE 1

This example illustrates that DNA can be purified from bacterial lysates independently of the method used to prepare the DNA and without prior phenol extraction to remove proteins.

The diatomaceous earth slurry was prepared from 50 mg of Celite Super-Fine Super Floss in 0.5 mL of water.

One sample of DNA was prepared from 10 ml of overnight cultures using Triton-lysozyme lysis, followed by centrifugation of the chromosomal-membrane pellet. The supernatant was then precipitated with ethanol and dried.

In a second sample of DNA prepared from 10 ml of overnight cultures, the cells were lysed using SDS/NaOH. The mixture was then adjusted to pH 5 with potassium acetate and centrifuged to sediment most of the chromosomal DNA along with some protein. The resulting supernatant was precipitated once with isopropanol and dried.

Each of the above dried DNA samples was resuspended in TE and diluted with $NaClO_4$ buffer. Varying quantities of Celite slurry were then added and the mixtures were mixed at RT for 15 min., after which they were microfuged and the supernatant discarded. The pellets were washed twice with $NaClO_4$ buffer, then twice with 50% washing buffer. The liquid was removed and the DNA eluted in TE. DNAs from the eluted fractions were then subjected to restriction digestion with PstI and to subsequent ligation with DNA ligase, following standard procedures.

The results show that DNAs prepared by both procedures and purified on diatomaceous earth are free of RNA, are readily restrictable and appear fully ligatable.

EXAMPLE 2

This example illustrates the scaleup of purification of larger quantities of plasmid.

Both pRSVcat and pBR322 plasmids were used in this example.

The diatomaceous earth slurry used was 50 mg of Celite Super-Fine Super Floss in 0.5 mL of water.

Following the procedures of Example 1, the plasmids were prepared and were purified by binding to Celite, using the amounts of components as shown in Table A. The DNAs eluted from the 100 µg samples of pRSVcat and pBR322 were analyzed on agarose gel and were shown to be of comparable quality to the small-scale preparations of Example 1.

TABLE A

| EXAMPLES OF SCALE-UP | | | | | |
|---|---|---|---|---|---|
| DNA (µg) | Celite (µL) | A buffer (µL)[a] | B buffer (µL)[b] | TE (µL) | tube needed |
| 1 | 10 | 430 | 800 | 30 | 0.5 mL epp. |
| 10 | 100 | 1200 | 2000 | 300 | 1.5 mL epp. |
| 100 | 1000 | 12000 | 20000 | 3000 | 15 mL |

TABLE A-continued

| EXAMPLES OF SCALE-UP | | | | | |
|---|---|---|---|---|---|
| DNA (µg) | Celite (µL) | A buffer (µL)[a] | B buffer (µL)[b] | TE (µL) | tube needed |
| 500 | 15000 | 60000 | 120000 | 15000 | 50 mL |

[a] A Buffer: 6 M $NaClO_4$, 0.05 M Tris-Cl pH 8, 10 mM EDTA
[b] B Buffer: 20 mM Tris-Cl pH 7.5, 2 mM EDTA, 0.4 M NaCl, 50% ethanol

EXAMPLE 3

This example illustrates the transformation of *E. coli* cells with DNA purified by the process of the present invention.

Three different plasmids, pBR322 (standard cloning vector), pATH (a plasmid for overexpression of foreign proteins in *E. coli*) and pRSVcat (a plasmid containing a Rous Sarcoma Virus insert) were prepared from 10 ml cultures of *E. coli* HB101 cells (see, Maniatis et al., supra. p. 504) using either the SDS/NaOH method or the rapid boiling method. Crude DNA was then purified on Celite following the procedures described hereinabove. Aliquots of the eluted purified DNA were digested with restriction endonucleases following known procedures and their concentrations estimated on a 1% agarose gel. Given amounts were then used to transform competent HB101 cells by procedures known in the art. The results are given in Table B below. Also shown in the table are the efficiencies obtained with CsCl-purified pBR322, which is outside the scope of the present invention, and with pBR322 retrieved from an agarose gel by the procedures of Example 4. The data show that plasmids purified by the process of the invention are capable of conferring ampicillin resistance to cells originally lacking this genotype.

TABLE B

| DNA | Method of Extraction | DNA, ng | Colonies per ng of DNA |
|---|---|---|---|
| pBR322 | NaOH/SDS | 13.3 | 51 |
| pATH 3 | NaOH/SDS | 133.0 | 25 |
| pRSVcat | NaOH/SDS | 67.0 | 26 |
| pBR322 | Boiling | 13.3 | 15 |
| pATH 3 | Boiling | 133.0 | 60 |
| pRSVcat | Boiling | 67.0 | 16 |
| none | — | — | 0 |
| pBR322 | CsCl purified | 100.0 | 43 |
| pBR322 | isolated - agarose gel | 85.0 | 22 |

EXAMPLE 4

This example illustrates the isolation of supercoiled DNA from an agarose gel by binding onto diatomaceous earth.

The diatomaceous earth slurry used in this experiment was 167 mg Celite Super-Fine Super Floss in 1 mL water.

A sample containing 0.5 µg of supercoiled pBR322 DNA was loaded into a well of an agarose gel (1% (w/v) agarose gel in TBE buffer) using 2 µL 80% glycerol per 18 µL sample per well. A marker sample containing dye was placed in an adjacent lane to monitor the progress of the electrophoresis. The gel was run in TBE buffer for 120 min. at 50 V, after which the gel was placed in a solution of 1 µg/mL ethidium bromide and stained for 10 min. The DNA band of interest was then located by UV and that part of the gel containing the band was excised.

The piece of agarose gel containing the band of DNA was mixed with NaClO4 buffer (three times the volume of DNA solution plus slurry) at 37° C. with mixing until the gel was dissolved. The Celite slurry (10 μL) was added and the suspension was incubated for 10 min. at RT with mixing, after which it was microfuged for 30 sec. The binding and elution procedures were continued following those hereinabove.

Standards ranging from 5 to 20 μg/mL were applied to an agarose gel along with the recovered fraction of DNA. The results show recovery to be near quantitative.

The eluted DNA was successfully digested with six different enzymes having sites in the plasmid (PvuII, EcoRI, HindIII, BamHI, SalI and PstI). This shows that the ethidium bromide present in the original agarose gel band was effectively removed during the purification process, since intercalated ethidium bromide will inhibit restriction enzyme digestion of DNA. The DNA was also suitable for the transformation of competent cells (see Table B, last entry).

EXAMPLE 5

This illustrates that nucleoside triphosphates are effectively removed from radiolabeling reactions by the process of the present invention.

Lambda DNA (1 mg/mL) digested with HindIII was end-labeled with α-$^{35}$S-dATP using terminal transferase in the absence (Reaction A) or presence (Reaction B) of SDS, following standard procedures in the art. Following incubation at 37° C. for 4 hr., each reaction was then purified on Celite by solution binding following the procedures hereinabove, and then eluted into 100 μL of TE. Reaction B represents a control for nonspecific binding of the radiolabel since SDS will inhibit the labeling reaction. Aliquots of the eluent were counted for radioactivity, with the results given in Table C below. The input cpm in each reaction was 288,640 cpm and the background was 30 cpm. The results show that at least 99.4% of the radiolabel was removed by the purification process, while a 50% incorporation of the radiolabel into the DNA was observed.

TABLE C

| Rxn | DNA (μL) | 10X Buffer | en-zyme (μL) | water (μL) | dATP (μL) | 10% SDS (1 μL) | cpm per reaction |
|---|---|---|---|---|---|---|---|
| A | 3.2 | 0.6 | 1 | 0.2 | 1 | — | 244,000 |
| B | 3.2 | 0.6 | 1 | — | 1 | + | 1,564 |

EXAMPLE 6

This example illustrates the removal of linkers from cloning reactions using the process of the present invention.

A 14-mer self-complementary double-stranded DNA linker (25 μg) with the sequence CATGCCATG-GCATG was mixed with Celite (125 μL) in NaClO4 buffer following the procedures hereinabove. The binding and elution were monitored by $^{260}$A. The results showed that no binding or elution of the linker was detected.

EXAMPLE 7

This example illustrates the binding and elution of a spectrum of linear fragments of DNA.

Linearized lambda DNA fragments, ranging in size from 2 to 23 Kbp, were resolved on an agarose gel, cut out, and purified with Celite following the procedure of Example 4. All of the fragments were recovered in good yield from the agarose, and each digested well with a restriction endonuclease and ligated with T4 DNA ligase.

EXAMPLE 8

This example illustrates the binding and elution of a spectrum of supercoiled DNAs, including both single-stranded and double-stranded.

A single-stranded plasmid (M13mp19+strand, 7250 bp) and an array or ladder of double-stranded DNA (ranging from 2 to 16 Kbp) were each bound to and eluted from Celite following the procedures hereinabove. One μg of DNA was used in each case, and in each case all of the DNA was bound and the eluted fractions showed excellent yields.

EXAMPLE 9

This example illustrates the adsorption and release of plasmid DNA onto various silicas.

The diatomaceous earth used in this example was Celite Filteraid, or Celite 545. To obtain ground GF/C, Whatman GF/C glass filter disks were ground as described by Vogelstein et al. (supra), the disclosure of which is incorporated herein by reference. Silica slurry (Glassmilk TM) was used in this example as it came from the Geneclean kit (BIO 101, La Jolla, Calif.). The ground GF/C filter disks and the Glassmilk silica slurry are outside the scope of the present invention.

The plasmid DNA used in these experiments was pRSVcat. This plasmid contains the ori and amp genes of pBR322 along with a chloramphenicol acetyl transferase (cat) gene under control of the Rous Sarcoma Virus (RSV) long terminal repeats. Crude plasmid DNA extracts were prepared by the method of Birnboim (supra) the disclosure of which is incorporated herein by reference, and contained plasmid DNA at a concentration of 1 μg per μL.

To 20 μL of plasmid DNA was added 50 μL of NaI and 20 μL of Celite 545 or of Geneclean Glassmilk or of ground GF/C. This mixture was mixed briefly and incubated at room temperature (RT) for 5 min. to allow binding. The mixture was then microfuged for 10 sec. and the supernatant was set aside. The pellet was washed two times with 1 mL of 50% washing buffer to remove the NaI, microfuging as above. The final pellet was eluted with water at RT for 5 sec., or at 55° C. for 5 sec.

The eluted samples were digested with BamHI or PstI for 1 hour at 37° C. according to the manufacturers' instructions. Following the digestion with PstI, samples were placed at 65° C. for 10 min., and were then religated using 1 unit of T4 ligase at RT for 1 hour.

Electrophoresis of samples was carried out at RT for 2 hours at 50 V using 1% agarose gels in TBE (0.089 M Tris-borate, and 0.008 M EDTA). Following electrophoresis, gels were transferred to an aqueous solution of ethidium bromide (1 μg/mL) and allowed to stain for 10-15 min. This time of staining does not require destaining in water. Gels were photographed on Polaroid 107 film using F4.5 for 5 sec.

The results show that the DNA bound to and released from each sample is free of RNA and is readily restrictable with BamHI restriction endonuclease. The samples ligated with T4 DNA ligase as well.

EXAMPLE 10

This example is an illustration of the increased capacity of diatomaceous earth for binding supercoiled DNA, according to the present invention, compared to that of Geneclean Glassmilk. The Glassmilk slurry is outside the scope of the present invention.

The diatomaceous earth slurry was prepared by mixing 167 mg of Celite Super-Fine Super Floss in 1 mL of water.

The supercoiled DNA was supercoiled pBR322.

Varying aliquots from equivalent slurries of either Celite Super-Fine Super Floss or Glassmilk were added to the DNA in an amount of $NaClO_4$ buffer equal to 3 times the combined volume of the slurry and the DNA solution. The mixtures were incubated, with mixing, at RT for about 15 min. for binding, after which the silicas were sedimented by microfuging and the supernatants were analyzed on agarose gel for unbound DNA. The results showed that 3 μL of Celite binds as much DNA as does 30 μL of Glassmilk (each with an equivalent settled volume to total volume slurry ratio). This indicates that the diatomaceous earth has about 10 times the binding capacity of ground glass.

EXAMPLE 11

This example illustrates the process of the present invention in a column format.

The diatomaceous earth used in this example was Celite Filteraid (Celite 545).

Crude plasmid DNA extracts were prepared by the method of Birnboim (supra), the disclosure of which is incorporated herein by reference, and contained plasmid DNA at a concentration of 1 μg per μL.

A column (1 × 10 cm) containing 100 mg (300 μL bed volume) of Celite 545 was washed with 5 mL of water under gravity. This step was employed to wash out small silica particles. The column was then washed with five volumes of a 70% solution of NaI in water. DNA (40 μL) was added to 120 μL of NaI, the mixture was allowed to percolate into the column, and binding was allowed to occur for 15 min. at RT. The column was washed with 70% NaI in water (3 × 250 μL), followed by 50% washing buffer (3 × 1 mL). After the last wash, the column was gently blown free of residual ethanol using compressed air. The column was then washed with water (3 × 250 μL). Fractions collected were analyzed for DNA and restricted with PstI, and the restricted products were religated using T4 DNA ligase, following known procedures. Samples were examined by agarose gel electrophoresis.

The results show that there is good recovery of the plasmid DNA in the eluted fractions. In addition, the purified DNA is readily cut with PstI, a restriction enzyme known for its sensitivity to impurities in DNA samples, and readily religated.

EXAMPLE 12

This example illustrates the purification of DNA using an entrapped membrane format. It also illustrates that double-stranded DNA prepared by the process of the invention may be directly sequenced.

To prepare crude DNA from cells, DNA was isolated from HB101 cells carrying the plasmid pRSVcat by alkaline extraction as follows. Cell pellets were resuspended in 20 mL of GET buffer (50 mM glucose, 25 mM Tris-Cl pH 8, 10 mM EDTA) and placed on ice for 5 min. To this was added 40 mL of 1% sodium dodecyl sulfate/0.2 M NaOH. and the mixture was gently inverted until clear. After incubation for 5 min. at RT, 38 mL of 3 M sodium acetate, pH 5.2, was added and the mixture was inverted gently for 15 min. The solution was then centrifuged at 18.000 × g for 30 min. and the supernatant was reserved. To the supernatant was added 0.7 volumes of isopropanol and mixed. After 10 min. at RT, the mixture was centrifuged as above and the supernatant was discarded. The pellet was dried briefly under vacuum in aliquots representing 125 mL of culture each.

A DNA pellet (representing 125 mL cells) was resuspended in 1-2 mL of TE at 37° C. for 15-20 min. To this solution was added three volumes of $NaClO_4$ binding buffer. Separately, a Teflon membrane-entrapped preparation of Celite Super-Fine Super Floss (prepared by the procedure of U.S. Pat. No. 4,153,661) was washed with 10 mL of water and then with 5 mL of $NaClO_4$ binding buffer. The DNA solution was passed across the membrane by syringe at about 1 mL/min. The membrane was then washed with 5 mL of $NaClO_4$ binding buffer and with 5 mL of 50% washing buffer. The membrane was purged by an air-filled syringe until no more liquid emerged. Next, the DNA was eluted from the membrane using 2 mL of TE, and an aliquot of 100 μL of the eluted DNA was taken to dryness under vacuum.

The purified DNA pellet was resuspended in 30 μL of TE and denatured using 10 μL of 0.4 M NaOH and 0.4 mM of EDTA for 5 min. at RT. To this DNA was added 2 μL of 2 M ammonium acetate, pH 4.5, and then 55 μL of ice cold ethanol. After incubation for 15 min. on dry ice, the sample was microfuged for 4 min. The pellet was washed with 40 μL of 70% ethanol and dried under vacuum.

Double-stranded sequencing of the DNA then followed, using the procedure of Zhang et al. (1988, Nucleic Acids Research 16:1220), the disclosure of which is incorporated herein by reference, with slight modification. The modification employed was the use of a heat-stable DNA polymerase Klenow fragment from the heat-resistant organism *Bacillus stearothermophilus* (supplied by Bio-Rad, Richmond. Calif.) and a reaction temperature of 65° C. Samples of the reaction were then applied to a standard DNA sequencing gel and electrophoresed for 4-5 hours at 3000 volts.

FIG. 1 presents the results of this sequencing reaction using pRSVcat purified above (gel B) compared with the same sequencing procedure using pBR322 (gel A) prepared using a prior art procedure of two sequential CsCl gradients for purification (available commercially from Bio-Rad. Richmond, Calif.). The sequence for the region of the gene common to both plasmids, the amp (ampicillin resistance) gene (primer is homologous to the PstI site, approximately 460 bases from the ATG initiation codon) can be clearly read from the bottom of each gel, beginning with TTAACTGGCG. The DNA prepared by the process of this invention can be successfully sequenced directly and is as pure as the DNA prepared by laborious CsCl gradient centrifugation.

What is claimed is:

1. In a process for the purification of DNA from a liquid mixture comprising such by:
   (a) combining said liquid mixture with a chaotropic agent and contacting the resulting combination mixture with silica by either forming a slurry of said combination mixture with silica, passing said combination mixture through a membrane in which silica is entrapped, or passing said combination mixture through an absorption column packed with silica, to selectively adsorb said DNA onto said silica, (b) washing said silica with a buffer containing from about 20% to about 95% of a lower alkyl alcohol to remove non-adsorbed matter, and (c) eluting said DNA from said silica with water or a low salt buffer, the improvement in which said silica is diatomaceous earth.

2. A process in accordance with claim 1 in which said chaotropic agent is a member selected from the group consisting of sodium iodide, sodium perchlorate and sodium trichlorate.

3. A process in accordance with claim 1 in which said lower alkyl alcohol is a member selected from the group consisting of methanol, ethanol and isopropanol.

4. A process in accordance with claim 1 in which said diatomaceous earth has an average particle size of less than about 125 microns.

5. A process in accordance with claim 4 in which said diatomaceous earth has an average particle size of less than about 50 microns.

6. A process in accordance with claim 5 in which said diatomaceous earth has an average particle size of from about 1 micron to about 10 microns.

* * * * *